(12) United States Patent
Akkermans et al.

(10) Patent No.: US 7,708,695 B2
(45) Date of Patent: May 4, 2010

(54) APPARATUS AND METHOD FOR DETECTING BLOOD FLOW

(75) Inventors: Antonius Hermanus Maria Akkermans, Eindhoven (NL); Carsten Heinks, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 468 days.

(21) Appl. No.: 11/568,395

(22) PCT Filed: Apr. 26, 2005

(86) PCT No.: PCT/IB2005/051356

§ 371 (c)(1), (2), (4) Date: Oct. 27, 2006

(87) PCT Pub. No.: WO2005/104935

PCT Pub. Date: Nov. 10, 2005

(65) Prior Publication Data

US 2008/0234590 A1 Sep. 25, 2008

(30) Foreign Application Priority Data

Apr. 29, 2004 (EP) .................... 04101817

(51) Int. Cl.
*A61B 5/02* (2006.01)

(52) U.S. Cl. .................................... 600/504

(58) Field of Classification Search .......... 600/504–507
See application file for complete search history.

(56) References Cited

U.S. PATENT DOCUMENTS

| | | | |
|---|---|---|---|
| 4,393,366 A | 7/1983 | Hill | |
| 4,699,149 A | 10/1987 | Rice | |
| 4,862,894 A | 9/1989 | Fujii | |
| 5,058,596 A * | 10/1991 | Makino et al. | 600/476 |
| 5,737,439 A * | 4/1998 | Lapsley et al. | 382/115 |
| 5,787,185 A | 7/1998 | Clayden | |
| 2002/0048014 A1 | 4/2002 | Kono et al. | |
| 2002/0104957 A1* | 8/2002 | Liess et al. | 250/221 |
| 2002/0183601 A1* | 12/2002 | Tearney et al. | 600/310 |
| 2003/0120156 A1* | 6/2003 | Forrester et al. | 600/473 |
| 2003/0236451 A1* | 12/2003 | El-Nokaly et al. | 600/300 |
| 2005/0157971 A1* | 7/2005 | Juijve et al. | 385/12 |

FOREIGN PATENT DOCUMENTS

JP 10127609 A 5/1998

(Continued)

OTHER PUBLICATIONS

Konishi et al. "Real-time visualization of retinal microcirculation by laser flowgraphy". Optical Engineering, Mar. 1995. vol. 34 No. 3. 753.*

(Continued)

*Primary Examiner*—Charles A Marmor, II
*Assistant Examiner*—Christian Y Jang

(57) ABSTRACT

A method and apparatus for detecting blood flow in or at a subject's fingertip (20) or other body part, in which Doppler-shifted measuring beam radiation (18) is reflected by the red blood cells and re-enters the laser cavity of the laser diode (10), so as to effect changes in operation thereof, such changes being representative of the blood flow. The apparatus may be incorporated in a fingerprint sensor as a "liveness" detector.

15 Claims, 2 Drawing Sheets

FOREIGN PATENT DOCUMENTS

WO    0237410 A1    5/2002

OTHER PUBLICATIONS

Figure 1:
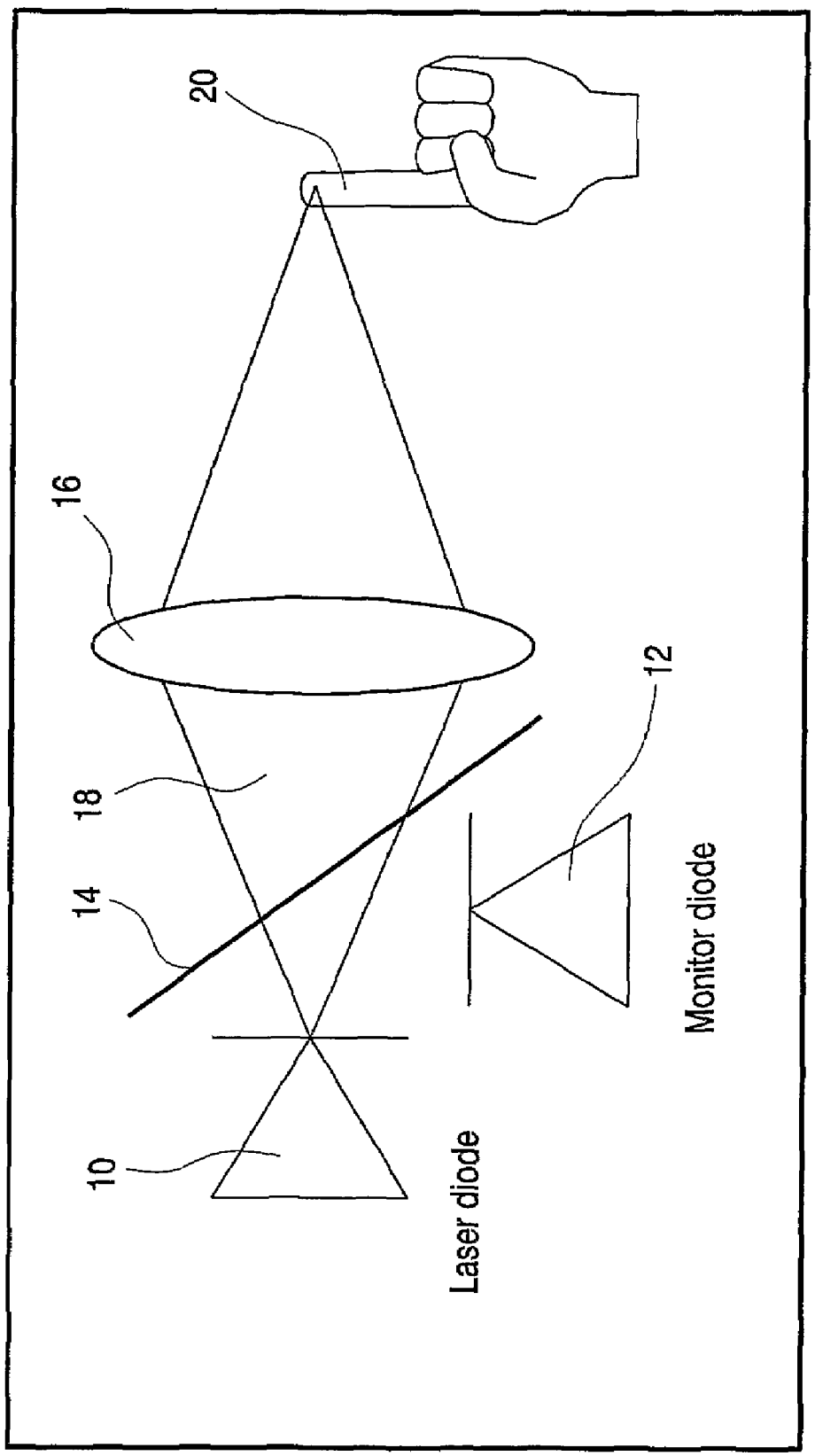

Sahin Kata Ozdemir, et al: Self-Mixing Laser Speckle Velocimeter for Blood Flow Measurement, IEEE vol. 49, No. 5, Oct. 2000, pp. 1029-1035.

Kalju Meigas, et al: Self-Mixing in a Diode Laser as a Method for Cardiovascular Diagnostics, J. Biomed Optics, vol. 8, No. 1, Jan. 2003, pp. 152-160, XP002331967.

Patent Abstracts of Japan, JP-A-10127609, Publication Date: May 19, 1998, Living Body Identifying Device, pp. 1-2.

Meigas Kalju et al; "Self-mixing in a diode laser as a method for cardiovascular diagnostics", Journal of Biomedical Optics, Jan. 2003, vol. 8 No. 1, pp. 152-160.

Ozdemir S.K. et al: "Self-mixing laser speckle velocimeter for blood flow measurement" IEEE Transactions on instrumentation and measurement, IEEE Inc. vol. 49, No. 5, Oct. 2000, pp. 1029-1035.

\* cited by examiner

APPARATUS AND METHOD FOR DETECTING BLOOD FLOW

CROSS REFERENCE TO RELATED APPLICATION

This application claims the benefit of European provisional application serial no. 04101817.7, filed Apr. 29, 2004, which the entire subject matter is incorporated herein by reference.

This invention relates to a method and apparatus for detecting blood flow in subcutaneous veins present at a portion of a user's body, wherein radiation is directed at the user's body portion, and radiation reflected thereby is received and analyzed.

Well-known biometric methods exist for identity verification and recognition, which are based on images of fingerprints, the iris, the face or recordings of speech. These recognition systems make use of a unique property of an individual that distinguishes them from other individuals. For example, in the arrangement described in U.S. Pat. No. 4,393,366, properties of the eye are used as a basis for recognition. However, this type of arrangement has been known to be susceptible to forgery by, for example, superimposing iris images over human eyes. Another known arrangement makes use of fingerprints, which are known to be a characteristic of a particular person—even identical twins possess different patterns. In any event, each of the known types of identity verification and recognition has both advantages and disadvantages in terms of convenience and intrusiveness. Fingerprint techniques in particular are very popular because of their user-friendliness and convenience. However, such techniques are very susceptible to forgery for two main reasons. Firstly, fingerprints are easy to replicate (in, for example, gelatin or the like) and secondly they can be relatively easily "stolen", even breathing on conventional fingerprint sensors can result in an erroneous verification.

It has been found that the pattern of subcutaneous blood vessels is characteristic of an individual and the fact that blood-vein patterns in the hand can be used as a unique "fingerprint" has been illustrated in U.S. Pat. No. 5,787,185. U.S. Pat. No. 4,699,149 describes apparatus for identifying an individual in which a user's body portion is irradiated by radiation to which the skin is translucent, and the location of blood vessels is detected by means of a differential temperature measurement, for example, or using techniques such as nuclear magnetic resonance or acoustic monitoring of the pulse.

However, even these types of systems are susceptible to forgery through the use of fake or non-living fingerprints.

It is therefore an object of the present invention to alleviate the problems outlined above, and provide apparatus for detecting blood flow in subcutaneous veins.

In accordance with the present invention, there is provided apparatus for detecting blood flow at a portion of a user's body, the apparatus comprising at least one laser, having a laser cavity, for generating a measuring beam arranged to be focused or converged at a point beneath the epidermis of said user's body portion, wherein at least some of the measuring beam radiation reflected by blood flowing in subcutaneous veins at said user's body portion re-enters said laser cavity, the apparatus further comprising measuring means for measuring changes in operation of said laser cavity caused by interference of reflected measuring beam radiation re-entering said laser cavity and the optical wave in said laser cavity, and means for providing an electric signal representative of said changes, said changes containing data relating to blood flow in said subcutaneous veins at said user's body portion.

The present invention extends to a heart rate monitor including apparatus for detecting blood flow as defined above.

Also in accordance with the present invention, there is provided a method for detecting blood flow at a portion of a user's body, the method comprising generating, using at least one laser having a laser cavity, a measuring beam arranged to be focused or converged at a point beneath the epidermis of said user's body portion, wherein at least some of the measuring beam radiation reflected by blood flowing in subcutaneous veins at said user's body portion re-enters said laser cavity, the method further comprising measuring changes in operation of said laser cavity caused by interference of reflected measuring beam radiation re-entering said laser cavity and the optical wave in said laser cavity, and providing an electric signal representative of said changes, said changes containing data relating to blood flow in said subcutaneous veins at said user's body portion.

Means may be provided for measuring a variation of impedance of the laser cavity. Alternatively, the measuring means may comprise a radiation detector for detecting radiation emitted by the laser.

In one embodiment, means may be provided for detecting blood flow at a plurality of positions within the user's body portion. For example, a plurality (e.g. a one- or two-dimensional array) of measuring means may be provided. Alternatively, or in addition, means may be provided for causing relative movement between the measuring beam and the user's body portion. In its simplest form, of course, this may be the ability to scan the user's body portion with the apparatus and/or the ability to allow the user to move, for example, their fingertip across a measurement area of the apparatus.

The measuring beam may comprise infra-red radiation, and the apparatus is preferably arranged and configured to detect blood flow in multiple directions. In one exemplary embodiment, a spectrum of reflected radiation may be generated and the apparatus beneficially comprises means for detecting the spectral width of reflected measuring beam radiation in order to identify blood flow in multiple directions.

The wavelength of the measuring beam radiation may be selected so as to penetrate the epidermis of the user's body portion to a predetermined depth. Optical means may alternatively, or in addition, be provided for focusing or converging the measuring beam radiation at the above-mentioned point beneath the epidermis of the user's body portion.

Imaging means may be provided for creating from the electric signal an image of one or more veins present in the user's body portion corresponding to the detected blood flow therein.

In one embodiment, the user's body portion may comprise a fingertip, and the present invention extends to a fingerprint detection system including apparatus for detecting blood flow, as defined above. The apparatus may be incorporated in a known fingerprint detection system to simply provide a "liveness" detector, i.e. if there is no blood flow, then the fingertip is not live.

Means may be provided for determining, from the detected blood flow, the user's heart rate and, in fact, as stated above, the invention extends to a heart rate monitor including apparatus for detecting blood flow as defined above.

These and other aspects of the present invention will be apparent from, and elucidated with reference to, the embodiment described herein.

Figure 2:
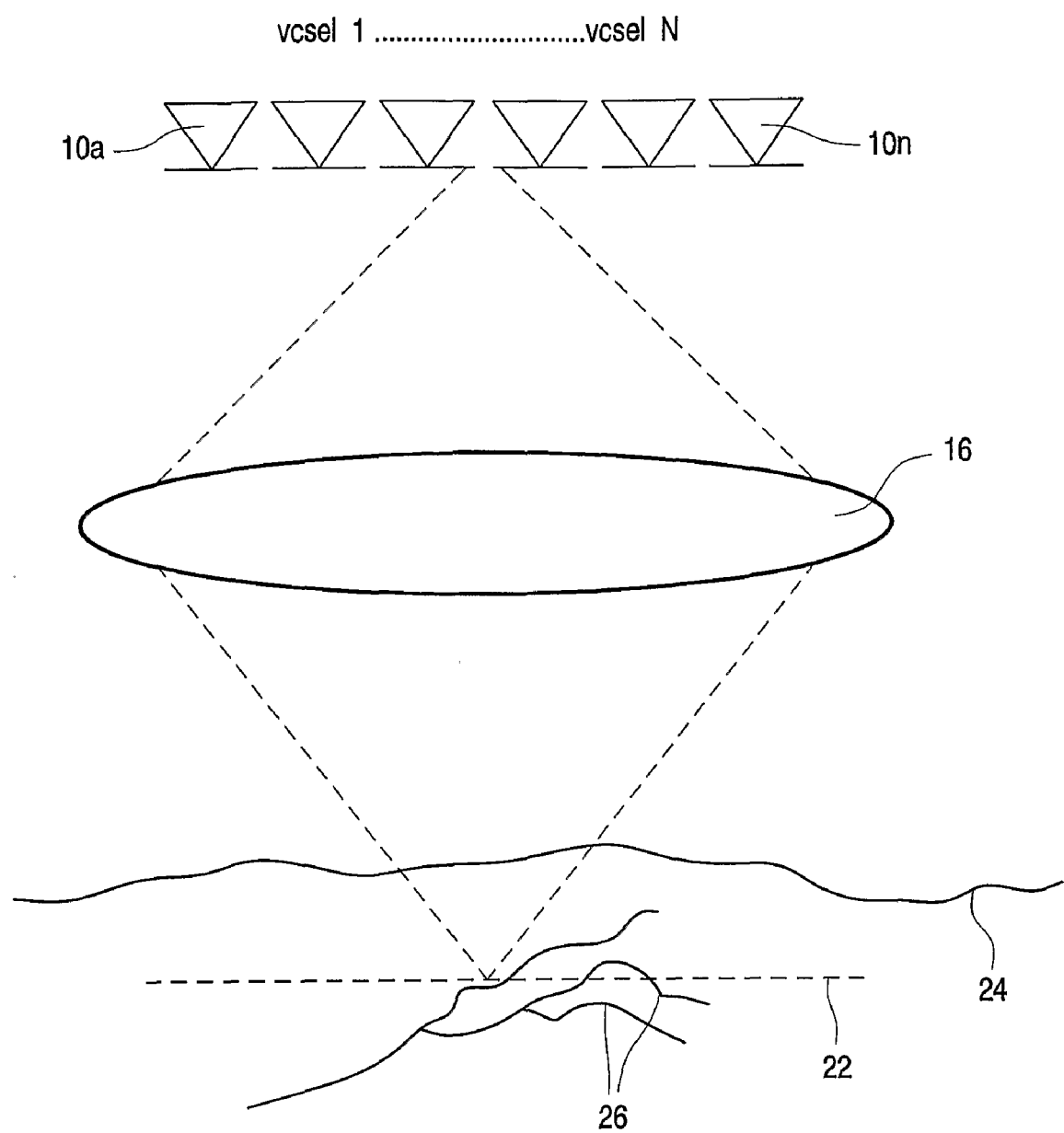

An embodiment of the present invention will now be described by way of example only and with reference to the accompanying drawings, in which:

FIG. 1 is a schematic diagram of a blood flow detector according to an exemplary embodiment of the present invention; and FIG. 2 is a schematic diagram of a blood flow detector according to another exemplary embodiment of the present invention, in which a one- or two-dimensional array of Doppler sensors is employed.

A phenomenon known as "self-mixing" in a laser diode is utilized in the present invention for the purposes of detecting blood flow. This phenomenon is used in a known arrangement for detecting movement of a fingertip relative to a sensor in an optical input device, as described in detail in International Patent Application No. WO 02/37410, wherein movement of the finger is detected to realize a mouse pad like function.

In the known arrangement, a diode laser having a laser cavity is provided for emitting a laser, or measuring, beam. At its upper side, the device is provided with a transparent window across which an object, for example a human finger, is moved. A lens, for example, a plano-convex lens is arranged between the diode laser and the window. This lens focuses the laser beam at or near the upper side of the transparent window. If an object is present at this position, it scatters the measuring beam. A part of the radiation of the measuring beam is scattered in the direction of the illumination beam and this part is converged by the lens on the emitting surface of the laser diode and re-enters the cavity of this laser. The radiation re-entering the cavity of the diode laser induces a variation in the gain of the laser and thus in the intensity of radiation emitted by the laser, and it is this phenomenon which is termed the self-mixing effect in a diode laser.

The change in intensity of the radiation emitted by the laser can be detected by a photo diode, provided for this purpose, which diode converts the radiation variation into an electric signal, and electronic circuitry is provided for processing this electric signal.

Movement of the object relative to the measuring beam causes the radiation reflected thereby to undergo a Doppler shift. This means that the frequency of this radiation changes or that a frequency shift occurs. This frequency shift is dependent on the velocity with which the object moves and is of the order of a few kHz to MHz. The frequency-shifted radiation re-entering the laser cavity interferes with the optical wave, or radiation generated in this cavity, i.e. a self-mixing effect occurs in this cavity. Dependent on the amount of phase shift between the optical wave and the radiation re-entering the cavity, the interference will be constructive or negative, i.e. the intensity of the laser radiation is increased or decreased periodically. The frequency of the laser radiation modulation generated in this way is exactly equal to the difference between the frequency of the optical wave in the cavity and that of the Doppler-shifted radiation re-entering the cavity. The frequency difference is of the order of a few kHz to MHz and thus easy to detect. The combination of the self-mixing effect and the Doppler shift causes a variation in behavior of the laser cavity; especially its gain or light amplification varies. The impedance of the laser cavity or the intensity of the radiation emitted by the laser may, for example, be measured, and not only can the amount of movement of the object relative to the sensor (i.e. distance traveled) be evaluated, but the direction of movement can also be determined, as described in detail in International Patent Application No. WO 02/37410.

Using the same principle, in accordance with the invention, by focusing the (preferably infra-red) laser beam deeper into the skin (i.e. under the epidermis) of, for example, a user's fingertip, blood flow in the subcutaneous blood vessels therein can be detected. The movement of red blood cells gives the reflected (infra-red) laser light the required Doppler shifts to cause the above-mentioned self-mixing effect in the laser cavity.

Referring to FIG. 1 of the drawings, in a first exemplary single-pixel system for detecting blood flow by means of laser Doppler shift, there is provided a laser diode 10, a monitor diode 12, a beam splitter 14 and a focusing lens 16 for focusing the radiation beam 18 emitted by the laser diode 10 to a point below the epidermis of a subject's fingertip 20. Coherent light reflected back and re-entering the laser cavity of the laser diode 10 will lead to a measurable intensity modulation of the laser caused by laser feedback and self-mixing, which can be measured using the monitor diode 12, and processed in the manner described above.

Current silicon integration technology enables the single-pixel detector size to be made very small and, accordingly, multiple such detectors could be integrated into a single integrated circuit to form, for example, a one- or two-dimensional array. In this way, an image of the blood vessels or veins located in the fingertip under consideration can be generated, but only if blood is flowing through these veins (because it is the movement created by such blood flow which creates the necessary Doppler shift). Of course it will be appreciated that this blood vein pattern, while unique and characteristic to each individual, cannot, unlike a normal fingerprint, be left behind on objects such as wine glasses, tables or keys. However, this also means that the so-called "fingerprint" provided by the above-mentioned blood vein pattern is very difficult to "steal".

Thus, as explained above, it is possible to generate a complete image of blood flow in the veins of an area of the subject's body under consideration (in this case, the fingertip), using a one-dimensional array of single-pixel detectors with relative movement of the array and the fingertip (either by scanning the stationary fingertip with the detector or moving the fingertip across the stationary array), or using a two-dimensional array of detectors (in which case, the fingertip can simply be placed relative to the array and both can be held stationary while the required measurements are carried out). In another exemplary embodiment, multiple photo diodes may be provided in respect of a single measuring beam to detect changes in the laser cavity caused by light reflected from different layers of veins beneath the subject's skin, although an adequate blood flow measurement could be obtained using a single photo diode appropriately located relative to the laser diode.

It will be appreciated by a person skilled in the art that, if the diode laser 10 of the arrangement of FIG. 1 is an edge emitting diode laser, then the beam splitter 14 is unnecessary because the monitor diode 12 is located behind the laser diode 10 and a [art of the light is emitted backwards. However, in the case of a VCSEL (Vertical Cavity Surface Emitting Laser), no light is emitted backwards. Therefore, a VCSEL and a separate photo diode may be placed in one housing, and although no beam splitter needs to be used, a housing output window is arranged and configured to reflect light onto the monitor diode.

The present invention can be used to provide a fingerprint sensor system in itself, which is very robust against forgeries. In addition, integrating a system, such as that illustrated schematically in FIG. 1 of the drawings, in a conventional fingerprint sensor results in a fingerprint sensor system which is more robust against security attacks and/or forgeries. In this case, the system of the invention is simply employed as a "liveness" detector, and the spot of the measuring beam is ideally positioned in the image field of the fingerprint, which can be realized either by using optical beam splitters or by integrating the liveness detector and fingerprint sensor into a single chip, for example.

The advantages associated with the present invention are numerous, and include the fact that the liveness detection is contactless and detects blood flow in and under the subject's skin. The system of FIG. 1 can be miniaturized and can therefore be made very small and at a very low cost. The laser diode 10, monitor diode 12 and signal processor can be integrated on silicon and the required lens can be, for example, glued on top of the chip. Thus, such a small-sized "liveness" detector can be relatively simply integrated into current solid state fingerprint sensors.

Furthermore, using conventional fingerprint sensing technology, fake (dead) fingerprints can be made fairly easily. However, simulating blood flow in and under the skin is more difficult. One way to (attempt to) simulate moving blood cells is by movement of the complete fingerprint. However, in this case, the image of the fingerprint is also moving and this can obviously be detected by the fingerprint sensor itself. The most likely outcome is that the fingerprint image becomes blurred because of the above-mentioned movement and fingerprint recognition fails.

Another way in which a conventional fingerprint recognition system can be attacked or tampered with is by moving a second layer on top of the fake fingerprint sample. If this simple, uni-directional movement, which results in a shift in the laser spectral peak, is detected by the liveness detector and the fake fingerprint is thin enough, then such a forgery might be successful. In order to block and defeat such an attack, the signal processing employed in the liveness detector may be arranged and configured such that it can discriminate between uni-directional movement and movement in many different directions, which is much more typical of the blood flow in a vein network. In general, such multiple movements will result in a widening of the laser spectral peak, which can be detected virtually instantaneously. Thus, it is possible for the system of the present invention (by relatively simple implementation of the signal processing) to distinguish between a single, one-directional movement (in the case of forgery), which results simply in a shift of the laser spectral peak, and a more complex pattern of multiple movements in the case of a genuine, live fingerprint, in which case there is a determinable widening of the laser spectral peak.

Referring to FIG. 2 of the drawings, in a second exemplary, multi-pixel system for detecting blood flow by means of laser Doppler shift, there is provided a one- or two-dimensional array of VCSEL diodes 10a-10n (numbered vcsel 1 ... N in the case of a one-dimensional array, or vcsel 1*1 ... n*m in the case of a two-dimensional array), and a focusing lens 16 for focusing the radiation beam 18 emitted by the laser diode 10 to an image plane 22 below the epidermis 24 of a subject's fingertip. Coherent light reflected back and re-entering the laser cavity of the laser diodes 10a-n will lead to a measurable intensity modulation of the laser caused by laser feedback and self-mixing dependent on blood flow in the veins 26, which intensity modulation can be measured and processed in the manner described above.

It should be noted that the above-mentioned embodiment illustrates rather than limits the invention, and that those skilled in the art will be capable of designing many alternative embodiments without departing from the scope of the invention as defined by the appended claims. In the claims, any reference signs placed in parentheses shall not be construed as limiting the claims. The word "comprising" and "comprises", and the like, does not exclude the presence of elements or steps other than those listed in any claim or the specification as a whole. The singular reference of an element does not exclude the plural reference of such elements and vice-versa. The invention may be implemented by means of hardware comprising several distinct elements, and by means of a suitably programmed computer. In a device claim enumerating several means, several of these means may be embodied by one and the same item of hardware. The mere fact that certain measures are recited in mutually different dependent claims does not indicate that a combination of these measures cannot be used to advantage.

The invention claimed is:

1. An apparatus comprising:
at least one laser, having a laser cavity, for generating a measuring beam arranged to be focused or converged at a point beneath the epidermis of said user's body portion, wherein at least some of the measuring beam radiation reflected by blood flowing in subcutaneous veins at said user's body portion re-enters said laser cavity,
measuring means for measuring changes in operation of said laser cavity caused by interference of the reflected measuring beam radiation re-entering said laser cavity and an optical wave in said laser cavity,
means for providing an electric signal representative of said changes, said changes containing data relating to blood flow in said subcutaneous veins at said user's body portion;
imaging means for creating from said electric signal, an image of one or more veins present in said user's body portion corresponding to said detected blood flow therein; and
a signal processor adapted to distinguish between changes in operation of the laser cavity caused by a unidirectional movement of the user's body portion and changes in operation of the laser cavity caused by the blood flow in the subcutaneous veins.

2. The apparatus of claim 1, wherein said measuring means comprise means for measuring a variation of the impedance of the laser cavity.

3. The apparatus of claim 1, wherein said measuring means comprise a radiation detector for detecting radiation emitted by said laser.

4. The apparatus of claim 1, wherein said measuring beam comprises infra-red laser radiation.

5. The apparatus of claim 1, wherein the wavelength of said measuring beam radiation is selected so as to penetrate the epidermis of said user's body portion to a predetermined depth.

6. The apparatus of claim 1, further comprising optical means for focusing or converging said measuring beam radiation at said point beneath the epidermis of said user's body portion.

7. A fingerprint detection system including the apparatus of claim 1.

8. The apparatus of claim 1, further comprising means for determining, from said detected blood flow, the user's heart rate.

9. A heart rate monitor including the apparatus of claim 8.

10. A method comprising:
generating, using at least one laser having a laser cavity, a measuring beam arranged to be focused or converged at a point beneath the epidermis of said user's body portion, wherein at least some of the measuring beam radiation reflected by blood flowing in subcutaneous veins at said user's body portion re-enters said laser cavity;

measuring changes in operation of said laser cavity caused by interference of the reflected measuring beam radiation re-entering said laser cavity and the optical wave in said laser cavity;

providing an electric signal representative of said changes, said changes containing data relating to blood flow in said subcutaneous veins at said user's body portion;

creating from said electric signal, an image of one or more veins present in said user's body portion corresponding to said detected blood flow therein; and distinguishing between changes in operation of the laser cavity caused by a unidirectional movement of the user's body portion and changes in operation of the laser cavity caused by the blood flow in the subcutaneous veins.

11. The method of claim 10, wherein the impedance of said laser cavity is measured.

12. The method of claim 10, wherein the intensity of said laser radiation is measured.

13. The apparatus of claim 1, further comprising a beam splitter for directing a portion of the measuring beam from the laser to the measuring means.

14. An apparatus comprising:

an array of laser cavities, for generating a measuring beam arranged to be focused or converged at a point beneath the epidermis of the user's body portion, wherein at least some of the measuring beam radiation reflected by blood flowing in subcutaneous veins at the user's body portion re-enters the laser cavities;

an array of monitor diodes for measuring changes in operation of the laser cavities caused by interference of the reflected measuring beam radiation re-entering the laser cavities and optical waves in the laser cavities;

means responsive to the measured changes in operation of the laser cavities for generating an image of one or more veins present in the user's body portion corresponding to the detected blood flow therein.

15. The apparatus of claim 14, further comprising a beam splitter for directing a portion of the measuring beam from the laser to the measuring means.

\* \* \* \* \*